United States Patent
Bagheri (10) Patent No.: US 10,130,443 B1
(45) Date of Patent: Nov. 20, 2018

(54) ENDODONTIC HAND FILE AND METHODS FOR ATTACHMENT

(71) Applicant: Moji Bagheri, Anaheim Hills, CA (US)

(72) Inventor: Moji Bagheri, Anaheim Hills, CA (US)

(*) Notice: Subject to any disclaimer, the term of this patent is extended or adjusted under 35 U.S.C. 154(b) by 0 days.

(21) Appl. No.: 15/598,950

(22) Filed: May 18, 2017

(51) Int. Cl.
*A61C 5/42* (2017.01)
*A61C 5/44* (2017.01)
*A61C 5/40* (2017.01)

(52) U.S. Cl.
CPC .............. *A61C 5/42* (2017.02); *A61C 5/44* (2017.02); *A61C 5/40* (2017.02)

(58) Field of Classification Search
CPC .... A61C 5/40; A61C 5/42; A61C 5/44; A61C 19/041; A61C 19/042; A61C 19/04
USPC ...................................................... 433/214, 2
See application file for complete search history.

(56) References Cited

U.S. PATENT DOCUMENTS

| | | | |
|---|---|---|---|
| 3,924,334 A * | 12/1975 | Lentine | A61C 5/44 279/43 |
| 4,028,810 A * | 6/1977 | Vice | A61C 5/44 433/102 |
| 4,364,730 A * | 12/1982 | Axelsson | A61C 5/42 433/141 |
| 5,092,769 A * | 3/1992 | Reiter | A61C 5/44 433/102 |
| 6,074,209 A | 6/2000 | Johnson | |
| 6,158,444 A | 12/2000 | Weihrauch | |
| 6,302,691 B1 * | 10/2001 | Manzoli | A61C 19/002 433/102 |
| 6,520,773 B1 * | 2/2003 | Weber | A61C 5/42 433/27 |
| D497,668 S | 10/2004 | Bogazzi | |
| 6,932,605 B2 | 8/2005 | McLean et al. | |
| 7,270,541 B1 | 9/2007 | Johnson | |
| 7,347,692 B2 | 3/2008 | Roetzer et al. | |
| D571,043 S | 6/2008 | Crossman | |
| 7,731,498 B2 | 6/2010 | McSpadden | |
| 7,766,657 B2 | 8/2010 | Jaunberzins | |
| 7,938,645 B2 | 5/2011 | Sapian | |
| 8,047,842 B2 | 11/2011 | Johnson | |
| 8,182,265 B2 | 5/2012 | McSpadden | |
| D662,206 S | 6/2012 | Way et al. | |

(Continued)

OTHER PUBLICATIONS

International Search Report & Written Opinion dated Jun. 29, 2018 from PCT Application No. PCT/US18/32591.

*Primary Examiner* — Nicholas Lucchesi
*Assistant Examiner* — Shannel Wright
(74) *Attorney, Agent, or Firm* — Innovation Capital Law Group, LLP; Vic Lin (57) ABSTRACT

A dental instrument is designed to help facilitate the procedure of root canal therapy and can reduce the inaccuracies that are accompanied with using traditional methods of attaching an electronic apex location (EAL) to an endodontic hand file. The endodontic hand file can include an exposed window in the handle of the file that holds an extension of the main body of the file. The clasp from the EAL can attach to this exposed metal in the window of the handle. This new location for attaching the EAL to the hand file can provide an accurate measurement while removing variables such as file movement in the canal, stopper thickness, clearance from the opposing tooth. The endodontic hand file with its exposed window provides a safe, reliable and accurate way of using an EAL to measure the root canal length.

17 Claims, 9 Drawing Sheets

(56) References Cited

U.S. PATENT DOCUMENTS

| | | |
|---|---|---|
| D668,339 S | 10/2012 | Luoto |
| D674,610 S | 1/2013 | Eatherton |
| D679,837 S | 4/2013 | Bonjar |
| D700,329 S | 2/2014 | Lim |
| 8,647,116 B2 | 2/2014 | Becker et al. |
| 8,727,772 B2 | 5/2014 | Jaunberzins |
| D710,009 S | 7/2014 | Maupin |
| 8,790,116 B2 | 7/2014 | Becker et al. |
| D714,114 S | 9/2014 | Robinson et al. |
| D737,443 S | 8/2015 | Ciravolo et al. |
| D742,007 S | 10/2015 | Schuetz |
| D744,101 S | 11/2015 | Kiefer et al. |
| D747,842 S | 1/2016 | Bressler |
| D764,103 S | 8/2016 | Wallström et al. |
| D767,900 S | 10/2016 | Kalbfeld |
| 2005/0003326 A1* | 1/2005 | Lampert ............... A61C 19/041 433/102 |
| 2007/0218420 A1* | 9/2007 | Syribeys ............... A61C 19/041 433/32 |
| 2009/0181341 A1* | 7/2009 | Lampert ............... A61C 19/041 433/102 |
| 2012/0308957 A1* | 12/2012 | Katoh ....................... A61C 5/42 433/102 |
| 2015/0230902 A1* | 8/2015 | Andreou ............... A61C 19/041 433/27 |
| 2015/0282601 A1 | 10/2015 | Butz et al. |
| 2016/0302883 A1 | 10/2016 | Sprechman |

* cited by examiner

ENDODONTIC HAND FILE AND METHODS FOR ATTACHMENT

BACKGROUND OF THE INVENTION

1. Field of the Invention

One or more embodiments of the invention relates generally to endodontic tools. More particularly, the invention relates to an endodontic hand file having an exposed window in its handle for attachment to an electronic apex locator.

2. Description of Prior Art and Related Information

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Figure 1:
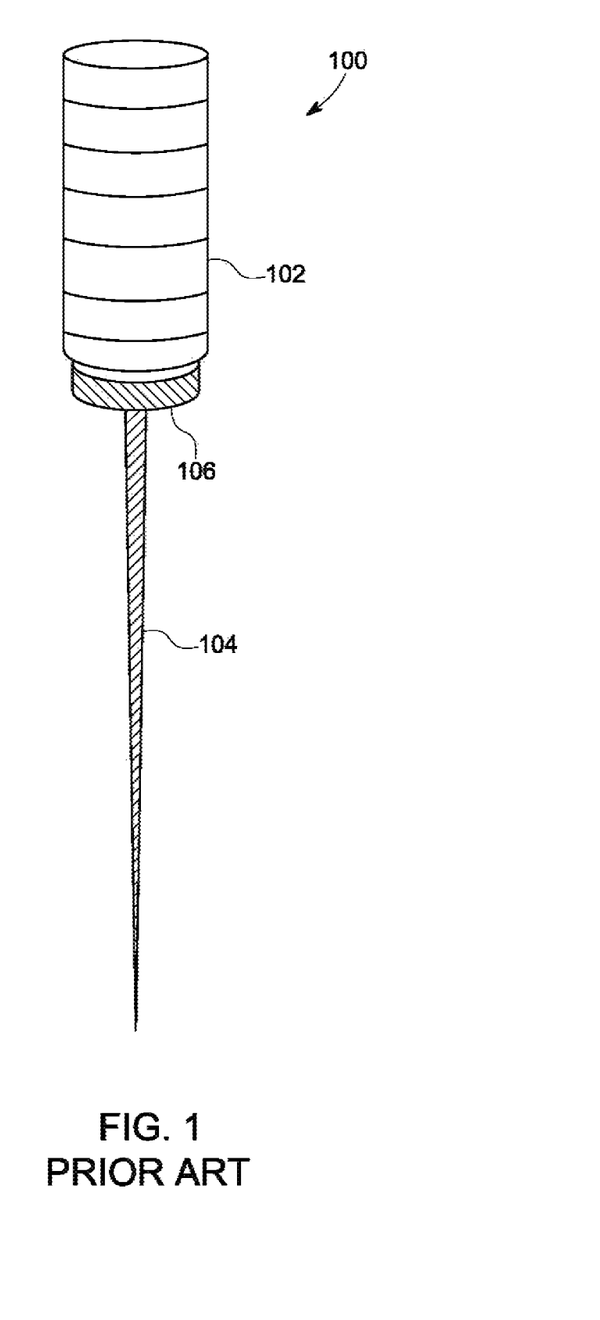
FIG. 1 illustrates a conventional endodontic hand file used in root canal therapy.

Referring to FIG. 1, an endodontic hand file 100 has a metal shaft 104 and a plastic handle 102. Such hand files 100 are commonly used to measure the length of a root canal in a tooth with the aid of an electronic apex locator (EAL). This instrument, due to its fine point and size, is able to enter and penetrate the root canal of a tooth and reach the end of the root "apex" via negotiations that are done along the way inside of the canal. Once the endodontic hand file reaches the terminus of the canal, it is able to act like a measuring device. This measurement can be accomplished by placing the endodontic hand file in the root canal and then attaching a connector from the EAL to the metal shaft of the file to complete an electronic circuit. The EAL is a digital machine that, in turn, can give a reading based on the position of the endodontic hand file and hence calculate the length of the root canal from an arbitrary point on the surface of the tooth to the terminus of the canal where the file tip is located.

One problem commonly encountered by conventional endodontic hand files 100 is one of access to its metal shaft 104. Currently, the best way to attach the EAL to the file is by means of a clasp, which is at one end attached to the EAL and at the other end to the metal shaft 104 of the file. This method of measurement brings its own set of problems and inaccuracies when the length of the root is close to the length of the file. The files are manufactured with three lengths—21 mm, 25 mm and 31 mm, which is standard of any file used in the field of endodontics. There is also a plastic stopper 106, about 2 mm thick, on the body of the file to facilitate the measurement. The most common problem and challenge faced by a user when using such files is when the root length is approximately the same as the file length, meaning that if the root canal length is 20.5 mm, a standard 21 mm file cannot be used to measure such length, as the actual working length is just shy of 20 mm. Should the user switch the file to a longer one, for example, a 25 mm file, it may be too long and not fit in the small working area within the surface of the tooth.

Moreover, when endodontics is performed on teeth with metal crowns, the metal shaft of the endodontic hand file can contact the metal restoration, creating a problem with canal measurement. Insulating sheaths can be used to cover the file shaft, but they may also limit access to the file shaft for contact with the EAL probe.

In view of the foregoing, there is a need for improved dental instruments to help facilitate the procedure of root canal therapy.

SUMMARY OF THE INVENTION

Embodiments of the present invention provide an endodontic hand file comprising a handle; a file having a first portion extending from the handle, and a second portion extending into the handle; a window formed in a portion of the handle; and an exposed portion of the second portion of the file passing into the window.

Embodiments of the present invention further provide an endodontic hand file comprising a handle; a file having a first portion extending from the handle, and a second portion extending into the handle; a window formed in a portion of the handle; and an exposed portion of the second portion of the file passing into the window, wherein the first portion and second portion of the file are formed integrally; and the second portion of the file includes a jog toward an exterior of the handle inside the handle before the exposed portion extends into the window.

Embodiments of the present invention also provide an endodontic hand file comprising a handle; a file having a first portion extending from the handle, and a second portion extending into the handle; a window formed in a portion of the handle; an exposed portion of the second portion of the file passing through the window and terminating with an extension portion disposed within the handle, wherein the first portion and second portion of the file are formed integrally; the second portion of the file includes a jog toward an exterior of the handle inside the handle before the exposed portion extends into the window; and a space is formed entirely about the exposed portion.

In some embodiments, the longitudinal axis of the exposed portion is substantially parallel to the longitudinal axis of the first portion of the file.

In some embodiments, the extension portion is angled toward the longitudinal axis of the first portion of the file.

In some embodiments, the window is formed as an indentation into the handle of the file.

In some embodiments, the depth of the indentation is less than about 50% of the thickness of the handle.

These and other features, aspects and advantages of the present invention will become better understood with reference to the following drawings, description and claims.

BRIEF DESCRIPTION OF THE DRAWINGS

Some embodiments of the present invention are illustrated as an example and are not limited by the figures of the accompanying drawings, in which like references may indicate similar elements.

Unless otherwise indicated illustrations in the figures are not necessarily drawn to scale.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention, and is not intended to limit the invention to the specific embodiments illustrated by the figures or description below.

As is well known to those skilled in the art, many careful considerations and compromises typically must be made when designing for the optimal configuration of a commercial implementation of any device, and in particular, the embodiments of the present invention. A commercial implementation in accordance with the spirit and teachings of the present invention may be configured according to the needs of the particular application, whereby any aspect(s), feature (s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

Broadly, embodiments of the present invention provide a dental instrument designed to help facilitate the procedure of root canal therapy. The dental instrument can reduce the inaccuracies that are accompanied using traditional methods of attaching an electronic apex location (EAL) to an endodontic hand file. The endodontic hand file can include an exposed window in the handle of the file that holds an extension of the main body of the file. The clasp from the EAL can attach to this exposed metal in the window of the handle. This new location for attaching the EAL to the hand file can provide an accurate measurement while removing variables such as file movement in the canal, stopper thickness, clearance from the opposing tooth. The endodontic hand file with its exposed window provides a safe, reliable and accurate way of using an EAL to measure the root canal length.

Figure 2:
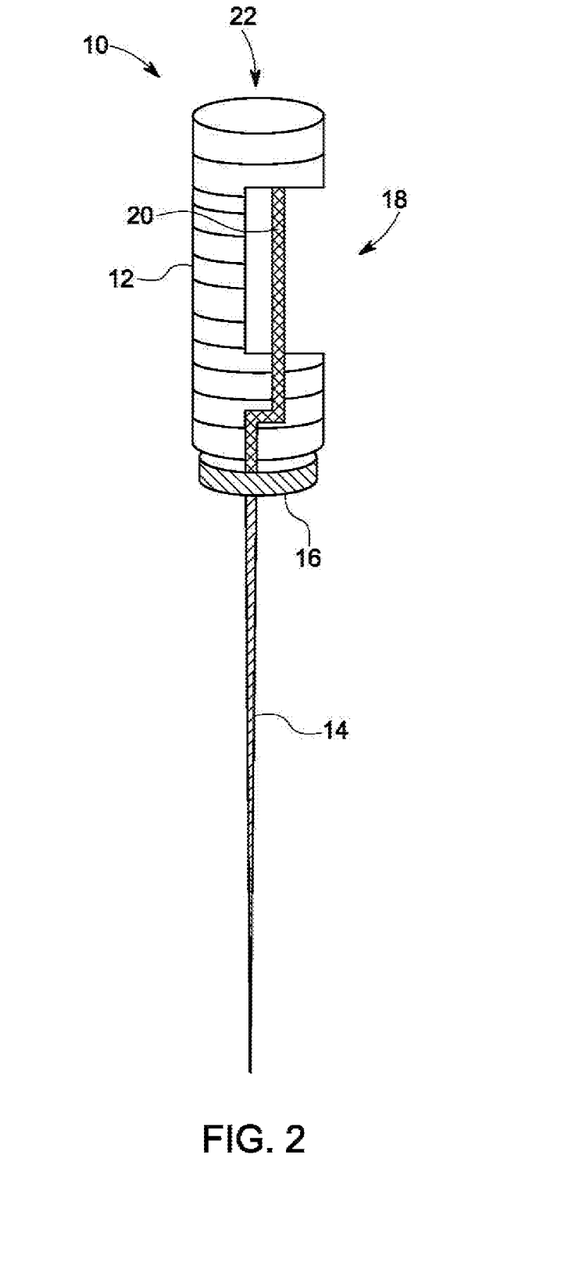
FIG. 2 illustrates a partially cut away view of an endodontic hand file according to an exemplary embodiment of the present invention.
Figure 2A:
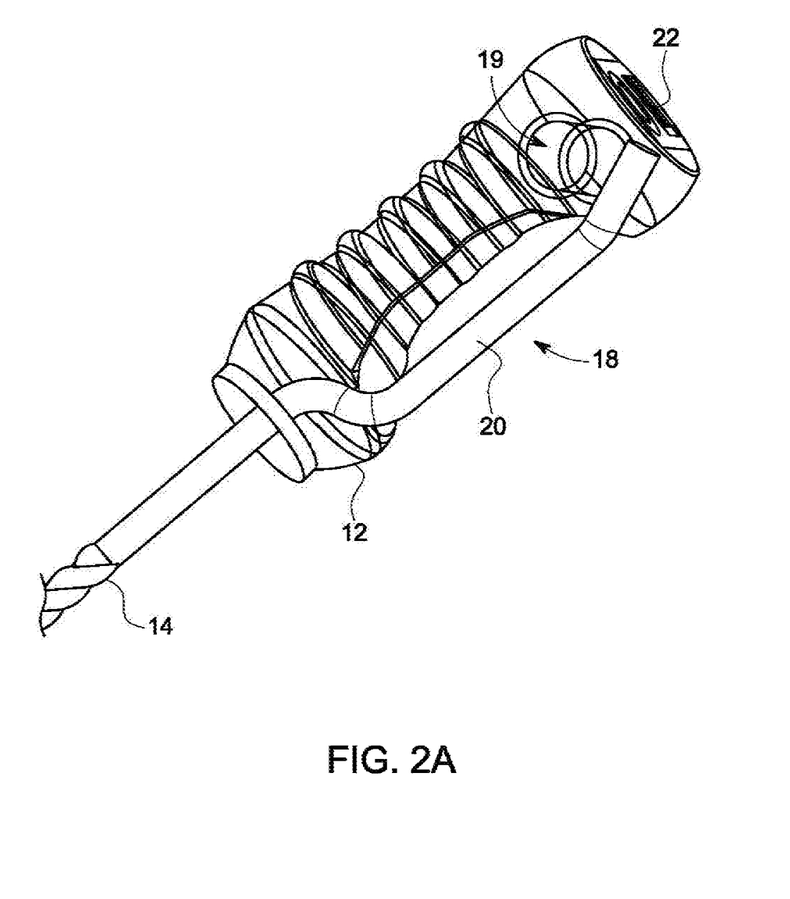
FIG. 2A illustrates a detailed view of the handle of the endodontic hand file of FIG. 2, with the body of the handle shown in shadow to illustrate the extension of the metal shaft therethrough.

Referring to FIGS. 2 and 2A, an endodontic hand file 10, also referred to as hand file 10 or simply file 10, includes a handle 12 and a metal file 14 extending from the handle 12. The metal file 14 extends into the handle 12 and further extends along a lengthwise axis thereof. The file 10 includes a window 18 cut into the handle 12 to expose a portion of the metal file 14 that extends into the handle 12. A stopper 16 may be disposed about the metal file 14, abutting the handle 12. A top portion 22 of the hand file 10 can include indicia to indicate the size of the hand file 10. These indicia may coordinate with currently used indicia used on conventional hand files 100, permitting the user to quickly and easily integrate the hand files 10 of the present invention into their practice. The hand file 10 may further include a hole 19 formed in the handle 12, similar to conventional hand files.

Figure 3:
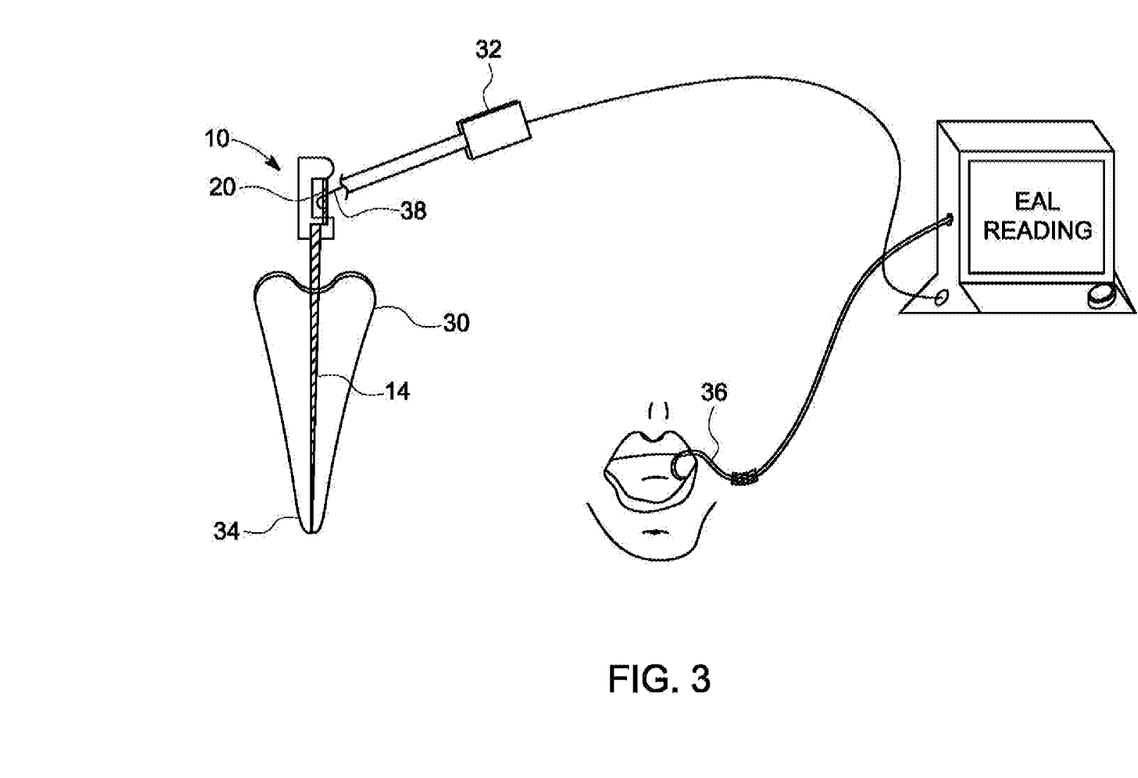
FIG. 3 illustrates a schematic representation of the endodontic hand file of FIG. 2 is use with an electronic apex locator during root canal therapy on a patient.

Referring now to FIGS. 2A and 3, in use, the metal file 14 of the hand file 10 may be placed into the root canal of a tooth 30 so that the tip of the metal file 14 reaches the apex at a distal end 34 of the tooth 30. A clamp 38 formed on an end of an EAL clasp-to-file shank extension 32 can attached to an exposed portion 20 of the metal file 14 in the window 18 of the handle 12. Another connector 36 may be disposed within the mouth of a patient to complete the connections for the EAL. The exposed portion 20 may extend from a bottom portion 26 of the window 18, may continue up to a top portion 24 of the window 18 and may further extend through the top portion 24 into the handle 12.

Figure 4:
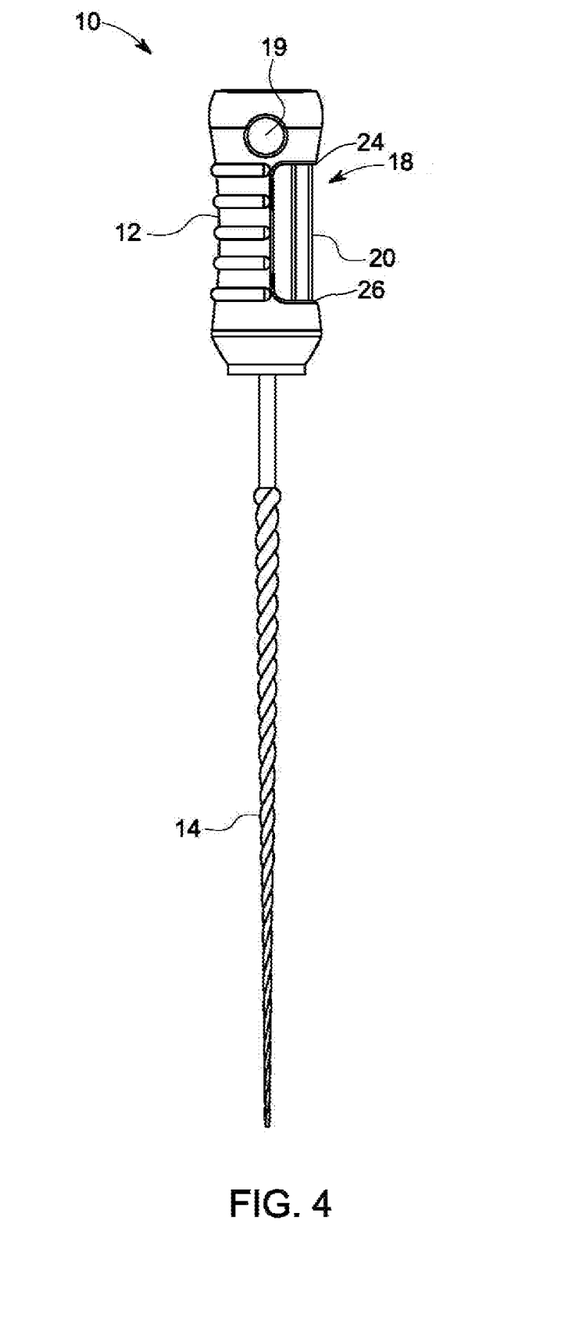
FIG. 4 illustrates a side view of an endodontic hand file according to an exemplary embodiment of the present invention.
Figure 5:
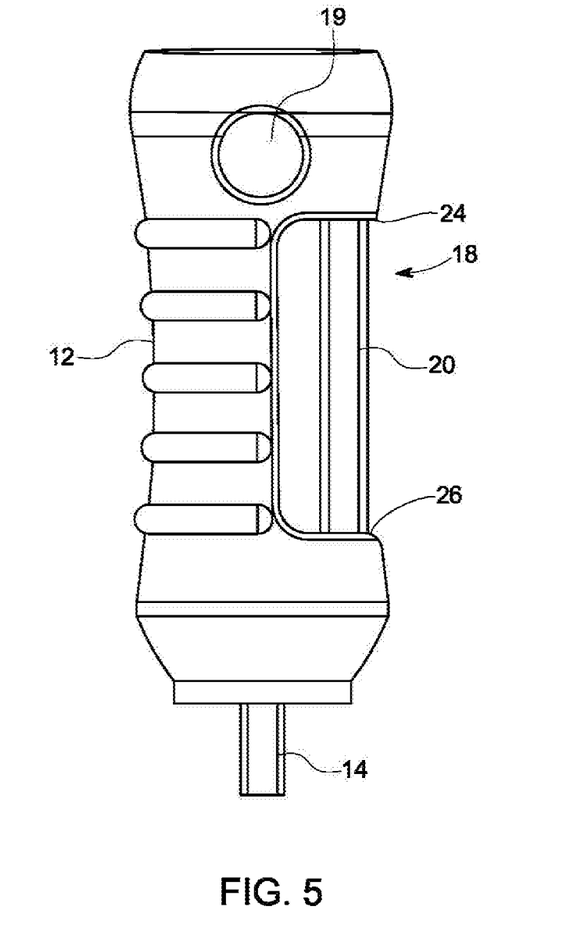
FIG. 5 illustrates a detailed view of the handle of the endodontic hand file of FIG. 4.

Referring now to FIGS. 4 and 5, the hand file 10 can take various shapes and sizes. Typically, the length and taper of the metal file 14 can correspond to conventional endodontic hand files. The handle 12 may also have a length similar to that of conventional hand files, such as from about 8 mm to about 12 mm, typically about 10 mm. The window 18 may have a length from about 3 mm to about 7 mm, typically about 4.85 mm. The depth of the window 18 may be from about 30% to about 60% of the depth of the thickness of the handle 12. In some embodiments, the depth of the window 18 may be less than about 50% of the thickness of the handle 12. In other words, the window 18 may cut into the handle 12 less than half of the handle's thickness.

Figure 6:
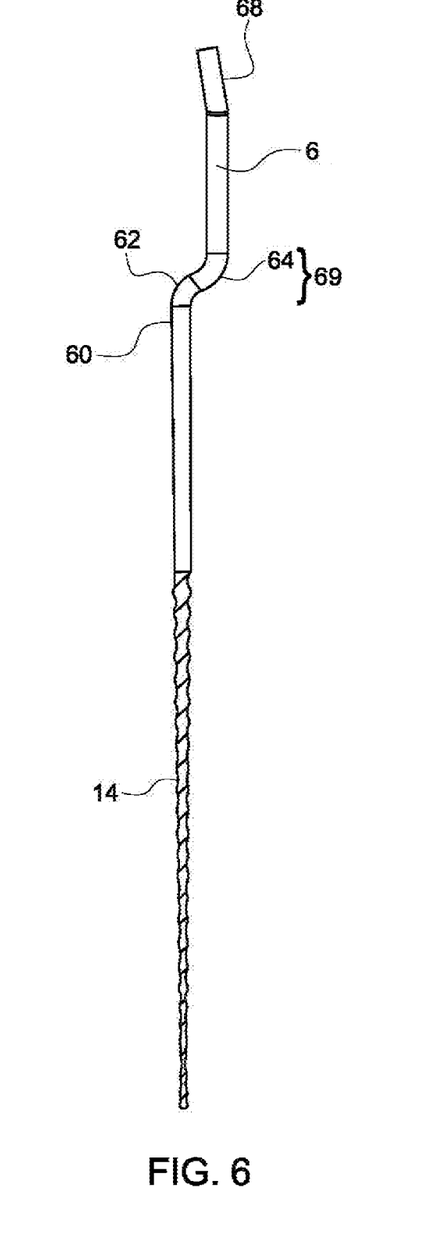
FIG. 6 illustrates a side view of the metal file and its extension into the file handle used in the endodontic hand file of FIG. 4.

Referring now additionally to FIG. 6, the metal file 14 may be formed as an integral unit. The handle 12 may be formed about the metal file 14 starting at location 60. In some embodiments, within the handle 12, the metal file 14 may jog in an elongated Z-pattern from about 1.0 mm to about 1.4 mm, typically about 1.2 mm. Typically, the amount of the jog is sufficient to permit a clasp (i.e., clasp 38, see FIG. 3) to fit on the exposed portion 20, with a space formed between the exposed portion 20 and the handle 12. This space may be from about 0.5 mm to about 0.9 mm, typically about 0.64 mm. In other words, the metal file may include a first bend 62 in a first direction, and a second bend 64 in a second direction, with a linear portion 66 extending from the second bend 64. The angles and orientation of the first bend 62 and the second bend 64 may be configured such that the linear portion 66 is substantially parallel with the metal file 14 that is inserted into the tooth's root canal, as previously illustrated and described. The first bend 62 and the second bend 64 combine to form jog 69, also referred to as offset 69. In some embodiments, the first bend 62 and the second bend 64 may form angles from about 20 to about 90 degrees, typically from about 30 to about 50 degrees. In some embodiments, a bend end portion 68 (also referred to as extension portion 68) may extend from the linear portion 66 of the metal file 14. This bent portion 68 may be angled inward, toward a longitudinal axis of the insertion portion of the metal file 14. The angle formed between the bent portion 68 and the linear portion 66 may be from about 5 to about 15 degrees, typically about 10 degrees.

Figure 7:
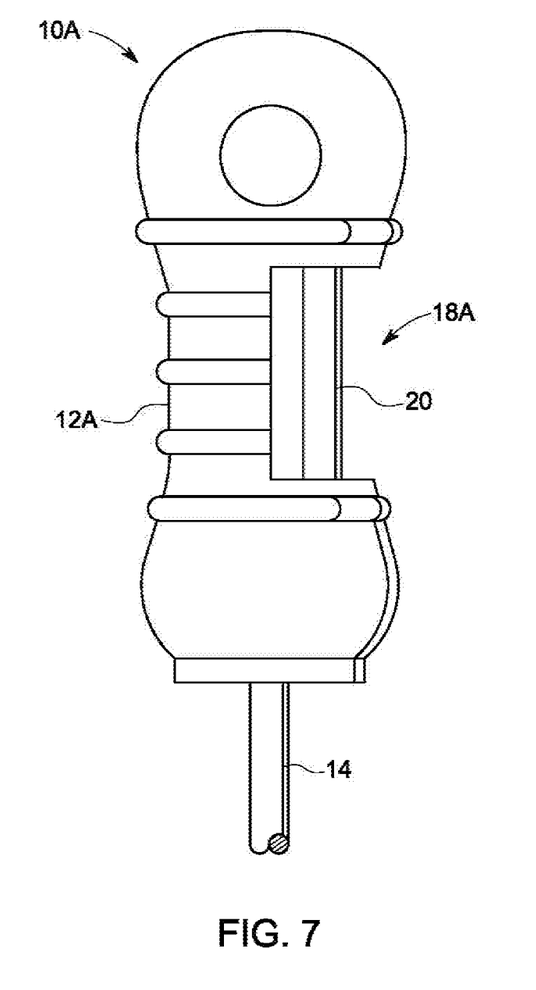
FIG. 7 illustrates a detailed side view of an endodontic hand file having an alternate handle shape, according to an exemplary embodiment of the present invention.

Referring now to FIG. 7, an endodontic hand file 10A may be formed in a more bulbous shape, where the handle 12A includes the window 18A, similar to that described above. FIG. 7 is just one example of various shapes for the handle 12, 12A, and other like shapes are contemplated within the scope of the present invention.

Figure 8:
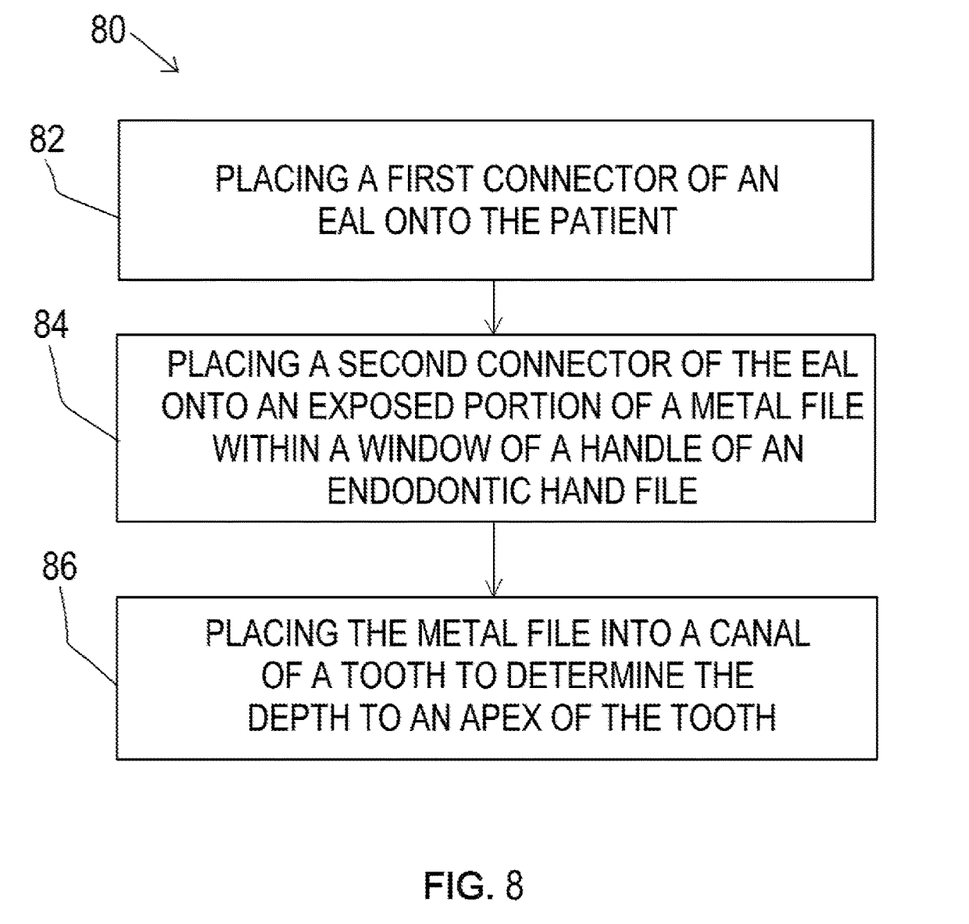
FIG. 8 illustrates a method for determining the depth of a tooth's root canal according to an exemplary embodiment of the present invention.

Referring now to FIG. 8, a method 80 for measuring a tooth canal depth may include a first step 82 of placing a first connector (i.e., connector 36) of an EAL onto the patient, such as on the patient's mouth or lip. A second step 84 includes placing a second connector (i.e., connector 38) of the EAL onto an exposed portion (i.e., exposed portion 20) of a metal file (i.e., metal file 14) within a window (i.e., window 18) of a handle (i.e., handle 12) of an endodontic hand file. The exposed portion is typically between a bottom of the handle and below a top of the handle. A further step 86 includes placing the metal file into a canal of a tooth to determine the depth to an apex of the tooth. These steps are performed in root canal therapy of a patient.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Claim elements and steps herein may have been numbered and/or lettered solely as an aid in readability and understanding. Any such numbering and lettering in itself is not intended to and should not be taken to indicate the ordering of elements and/or steps in the claims.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:

1. An endodontic hand file comprising:
 a handle;
 a file having a first portion extending from the handle, and a second portion extending into the handle;
 a window formed in a side portion of the handle;
 a first bend of the second portion bending the second portion toward an exterior of the handle, the first bend positioned within the handle;
 a second bend of the second portion bending the second portion toward a top end of the handle, the second bend positioned within the handle, the second bend positioned distal the first bend, relative to the first portion; and
 an exposed portion of the second portion of the file passing into the window, the exposed portion being distal the second bend, relative to the first portion, a longitudinal axis of the exposed portion being substantially parallel to a longitudinal axis of the first portion.

2. The endodontic hand file of claim 1, wherein the exposed portion of the file extends through the window and an extension portion of the file extends back into the handle.

3. The endodontic hand file of claim 2, wherein the extension portion is angled toward a longitudinal axis of the first portion of the file.

4. The endodontic hand file of claim 3, wherein an angle between the extension portion and the first portion is from about 5 to about 15 degrees.

5. The endodontic hand file of claim 1, wherein the exposed portion has a longitudinal axis that is offset from a longitudinal axis of the first portion of the file.

6. The endodontic hand file of claim 1, wherein the first portion and the second portion of the file are integrally formed.

7. The endodontic hand file of claim 1, wherein the window is formed as an indentation into the handle of the file.

8. The endodontic hand file of claim 7, wherein a depth of the indentation is less than about 50% of a thickness of the handle.

9. The endodontic hand file of claim 1, wherein a space is formed entirely about the exposed portion.

10. An endodontic hand file comprising:
a handle;
a file having a first portion extending from the handle, and a second portion extending into the handle;
a window formed in a portion of the handle; and
an exposed portion of the second portion of the file passing into the window, wherein
the first portion and second portion of the file are formed integrally;
the second portion of the file includes a jog toward an exterior of the handle, the jog being inside the handle before the exposed portion extends into the window; and
a longitudinal axis of the exposed portion is substantially parallel to a longitudinal axis of the first portion of the file.

11. The endodontic hand file of claim 10, wherein the exposed portion of the file extends through the window and an extension portion of the file extends back into the handle.

12. The endodontic hand file of claim 11, wherein the extension portion is angled toward a longitudinal axis of the first portion of the file.

13. The endodontic hand file of claim 10, wherein the window is formed as an indentation into the handle of the file.

14. The endodontic hand file of claim 13, wherein a depth of the indentation is less than about 50% of a thickness of the handle.

15. The endodontic hand file of claim 10, wherein a space is formed entirely about the exposed portion.

16. An endodontic hand file comprising:
a handle;
a file having a first portion extending from the handle, and a second portion extending into the handle;
a window formed in a portion of the handle;
an exposed portion of the second portion of the file passing through the window and terminating with an extension portion disposed within the handle, wherein
the first portion and second portion of the file are formed integrally;
the second portion of the file includes a jog toward an exterior of the handle, the jog positioned inside the handle before the exposed portion extends into the window;
a space is formed entirely about the exposed portion; and
a longitudinal axis of the exposed portion is substantially parallel to a longitudinal axis of the first portion of the file.

17. The endodontic hand file of claim 16, wherein the extension portion is angled toward a longitudinal axis of the first portion of the file.

* * * * *